US007927381B2

(12) United States Patent
Hercouet

(10) Patent No.: US 7,927,381 B2
(45) Date of Patent: Apr. 19, 2011

(54) PROCESS FOR LIGHTENING OR LIGHTENING DIRECT DYEING OR OXIDATION DYEING IN THE PRESENCE OF AN AQUEOUS COMPOSITION COMPRISING AT LEAST ONE FATTY SUBSTANCE, AND DEVICE

(75) Inventor: Leïla Hercouet, Neuilly Plaisance (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 12/642,551

(22) Filed: Dec. 18, 2009

(65) Prior Publication Data
US 2010/0223739 A1 Sep. 9, 2010

Related U.S. Application Data

(60) Provisional application No. 61/153,468, filed on Feb. 18, 2009, provisional application No. 61/151,618, filed on Feb. 11, 2009.

(30) Foreign Application Priority Data

Dec. 19, 2008 (FR) ...................................... 08 58880
Dec. 19, 2008 (FR) ...................................... 08 58888

(51) Int. Cl.
A61Q 5/10 (2006.01)
(52) U.S. Cl. ............. 8/405; 8/406; 8/435; 8/580; 8/602; 8/604; 8/619; 8/620; 132/202; 132/208
(58) Field of Classification Search ............... 8/405, 406, 8/435, 580, 602, 604, 619, 620; 132/202, 132/208
See application file for complete search history.

(56) References Cited

U.S. PATENT DOCUMENTS

| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie |
| 6,074,439 A | 6/2000 | De La Mettrie et al. |
| 6,129,770 A | 10/2000 | Deutz et al. |
| 6,156,713 A | 12/2000 | Colgate-Palmolive |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,766,977 B2 | 8/2010 | Cottard |
| 7,799,095 B2 | 9/2010 | Mario et al. |
| 2003/0190297 A1 | 10/2003 | Narasimham et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |

(Continued)

FOREIGN PATENT DOCUMENTS

CA 1 268 421 5/1990

(Continued)

OTHER PUBLICATIONS

French Search Report for FR 0858880, dated Sep. 18, 2009.

(Continued)

Primary Examiner — Eisa B Elhilo
(74) Attorney, Agent, or Firm — Finnegan Henderson Farabow Garret & Dunner, L.L.P.

(57) ABSTRACT

Provided is a process for lightening or dyeing keratin fibers, in which the following are applied to the said fibers: (a) an aqueous cosmetic composition (A) comprising at least one fatty substance and at least one surfactant; (b) a cosmetic composition (B) comprising at least one alkaline agent, (c) a cosmetic composition (C) comprising at least one oxidizing agent, wherein the amount of the at least one fatty substance in composition (A) is greater than 20% by weight relative to the total weight of composition (A), and when the process used is a process for dyeing keratin fibers, then cosmetic composition (B) further comprises at least one oxidation dye, at least one direct dye, or both. Also provided is a multi-compartment device.

15 Claims, No Drawings

U.S. PATENT DOCUMENTS

| | | |
|---|---|---|
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1* | 11/2006 | Legrand .................. 8/405 |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 A1 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 A1 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 A1 | 12/2001 |
| DE | 100 56 266 A1 | 5/2002 |
| DE | 101 48 571 | 4/2003 |
| DE | 101 48 671 A1 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 A1 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 A2 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 A1 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 A1 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

French Search Report for FR 0858888, dated Nov. 3, 2009.
English language abstract of DE 38 14 356 A1, Sep. 8, 1988.

English language abstract of DE 100 28 723 A1, Dec. 10, 2001.
English language abstract of DE 100 56 266 A1, May 23, 2002.
English language abstract of DE 101 48 671 A1, Apr. 10, 2003.
English language abstract of DE 197 12 980 A1, Oct. 1, 1998.
English language abstract of FR 2 910 309 A1, Jun. 27, 2008.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language Abstract of DE 101 48 571, dated Apr. 24, 2003.
English language Abstract of DE 195 27 121, dated Jan. 30, 1997.
English language Abstract of DE 197 23 538, dated Sep. 17, 1998.
English language Abstract of DE 199 62 869, dated Jun. 28, 2001.
English language Abstract of DE 43 09 509, dated Sep. 19, 1994.
English language Abstract of EP 1 023 891, dated Aug. 2, 2000.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Octoer 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58881, dated Sep. 29, 2009.
French Search Report for FR 08/58886, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.

Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

PROCESS FOR LIGHTENING OR LIGHTENING DIRECT DYEING OR OXIDATION DYEING IN THE PRESENCE OF AN AQUEOUS COMPOSITION COMPRISING AT LEAST ONE FATTY SUBSTANCE, AND DEVICE

This application claims benefit of U.S. Provisional Application Nos. 61/151,618, filed Feb. 11, 2009, and 61/153,468, filed Feb. 18, 2009. This application also claims benefit of priority under 35 U.S.C. §119 to French Patent Application Nos. 0858880 and 0858888, filed Dec. 19, 2008.

Provided is a process for lightening and for dyeing keratin fibers, in particular human keratin fibers such as hair, comprising the use of an aqueous cosmetic composition (A) comprising at least one fatty substance and at least one surfactant, of a cosmetic composition (B) comprising at least one alkaline agent, and of a cosmetic composition (C) comprising at least one oxidizing agent, when the process used is a process for dyeing keratin fibers, then the cosmetic composition (B) may also comprise at least one dye.

Also provided is a multi-compartment device comprising a first compartment comprising the above-mentioned aqueous cosmetic composition (A), a second compartment comprising the above-mentioned cosmetic composition (B), and a third compartment comprising the above-mentioned cosmetic composition (C).

For many years, people have sought to modify the color of their hair and to hide their grey hair. To do this, at least two types of coloration have been developed.

One type of coloration involves permanent dyeing or oxidation dyeing, using dye compositions comprising oxidation dye precursors, which may be known as oxidation bases. Those oxidation bases may be colorless or weakly colored compounds that, when combined with oxidizing products, can give rise, via a process of oxidative condensation, to colored compounds.

The shades obtained with those oxidation bases may often be varied by combining them with couplers or dye modifiers, which may be chosen from aromatic meta-diamines, meta-aminophenols, meta-diphenols, and heterocyclic compounds, such as indole compounds. The variety of molecules used as oxidation bases and couplers can allow a wide range of colors to be obtained.

Another type of dyeing involves semipermanent dyeing or direct dyeing, using dye compositions comprising direct dyes, which may comprise colored and coloring molecules having affinity for the fibers, leaving them on keratin fibers, for instance, for a time to allow the molecules to penetrate, by diffusion, into the fiber, and then rinsing them off.

To perform those dyeing operations, the direct dyes were often chosen from nitrobenzene, anthraquinone, nitropyridine, azo, xanthene, acridine, azine, and triarylmethane direct dyes.

That type of process does not require using an oxidizing agent to develop the coloration. However, it is not excluded to use one to obtain a lightening effect along with the coloration. Such a process may then be referred to as a direct dyeing or semipermanent dyeing under lightening conditions.

Processes of lightening or of permanent or semipermanent dyeing under lightening conditions thus use, along with the dye composition, an aqueous composition comprising at least one oxidizing agent, under alkaline pH conditions. The role of that oxidizing agent is believed to be, at least in part, to degrade the melanin of the hair, which, depending on the nature of the oxidizing agent present, may lead to more or less pronounced lightening of the fibers. Thus, for relatively weak lightening, the oxidizing agent may be hydrogen peroxide. When more substantial lightening is desired, peroxygenated salts, for instance persulfates, may be used in the presence of hydrogen peroxide.

One of the difficulties encountered when implementing the lightening and dyeing processes of the prior art may arise because those processes are performed under alkaline conditions and that the alkaline agent most commonly used is aqueous ammonia. Aqueous ammonia is believed to allow the pH of the composition to be adjusted to an alkaline pH to enable activation of the oxidizing agent. However, this alkaline agent also causes swelling of the keratin fiber, with raising of the scales, promoting the penetration of the oxidizing agent, and also, if they are present, of the dyes, for instance the oxidation dyes, into the fiber, increasing the efficacy of the dyeing reaction.

However, this alkaline agent is very volatile, which users find disagreeable due to the characteristic strong, rather unpleasant odor of ammonia that is given off during the process.

Furthermore, the amount of ammonia given off during the process makes it necessary to apply this alkaline agent in a larger amount than the amount required to form the process, to compensate for this loss. This is not without consequences on the user, who not only remains inconvenienced by the odor, but may also be confronted with greater risks of intolerance, for instance irritation of the scalp in the form, for instance, of stinging.

Replacing all or some of the aqueous ammonia with at least one other standard alkaline agents may lead to compositions that are less efficient than those based on aqueous ammonia, because those alkaline agents are not believed to afford sufficient lightening of pigmented fibers in the presence of the oxidizing agent.

Provided are lightening or dyeing processes of human keratin fibers performed in the presence of an oxidizing agent, which makes it possible to overcome at least one, and in certain embodiments all, of the aforementioned drawbacks.

Provided is a process for lightening or dyeing keratin fibers such as the hair, in which the following are applied to said fibers:

(a) an aqueous cosmetic composition (A) comprising at least one fatty substance and at least one surfactant;
(b) a cosmetic composition (B) comprising at least one alkaline agent;
(c) a cosmetic composition (C) comprising at least one oxidizing agent;

wherein the amount of the at least one fatty substance of composition (A) is greater than about 20% by weight relative to the total weight of composition (A), and when the process used is a process for dyeing keratin fibers, then the cosmetic composition (B) also comprises at least one oxidation dye, at least one direct dye, or both.

The lightening process described herein may, in some embodiments, make it possible to give the hair lightening performance qualities that are equivalent or even superior to those obtained with the existing compositions.

The dyeing process described herein, in some embodiments, may lead to strong, sparingly selective colorations, i.e. colorations that are uniform along the fiber.

Moreover, the processes described herein make it possible, in some embodiments, to produce compositions that do not give off an aggressive odor when they are applied to the hair or during their preparation.

Also provided is a multi-compartment device comprising, in a first compartment, an aqueous cosmetic composition (A) comprising at least one fatty substance and at least one surfactant, in a second compartment, a cosmetic composition (B) comprising at least one alkaline agent, and also optionally at least one oxidation dye, at least one direct dye, or both, and, in a third compartment, a cosmetic composition (C) comprising at least one oxidizing agent.

Other characteristics and advantages of the disclosure will emerge more clearly on reading the description and the examples that follow.

In the text hereinbelow, and unless otherwise indicated, the limits of a range of values are included in that range.

In some embodiments, the human keratin fibers treated by the process described herein are human hair.

In some embodiments, the process described herein is performed in the presence of an aqueous cosmetic composition (A) comprising at least one fatty substance.

In some embodiments, the amount of at least one fatty substance in the aqueous cosmetic composition (A) is greater than 20% by weight relative to the total weight of composition (A).

In some embodiments, the term "aqueous composition" means a composition comprising more than 5% by weight of water. In some embodiments, the term "aqueous composition" means a composition comprising more than 10% by weight of water. In some embodiments, the term "aqueous composition" means a composition comprising more than 20% by weight of water.

In some embodiments, the lightening process described herein is performed in the presence of compositions not comprising a direct dye or an oxidation dye precursor (bases and couplers). In some embodiments, the lightening process is performed in the presence of compositions comprising a direct dye or an oxidation dye precursor (bases and couplers), whose total content is less than 0.005% by weight relative to the weight of each composition. At such a content, only the composition would be optionally dyed, i.e. no coloration of the keratin fibers would be observed. In some embodiments, the lightening process described herein is performed without oxidation base, or coupler, or direct dye.

The at least one fatty substance describes an organic compound that is insoluble in water at ordinary ambient temperature (25° C.) and at atmospheric pressure (760 mmHg). In some embodiments, the at least one fatty substance has a water solubility of less than 5%. In some embodiments, the at least one fatty substance has a water solubility of less than 1%. In some embodiments, the at least one fatty substance has a water solubility of less than 0.1%. In some embodiments, the at least one fatty substance has a structure with at least two siloxane groups or one hydrocarbon-based chain comprising at least six carbon atoms. In some embodiments, the at least one fatty substance is soluble in organic solvents under the same temperature and pressure conditions, including but not limited to chloroform, ethanol, benzene, liquid petroleum jelly, and decamethyl cyclopentasiloxane.

Exemplary fatty substances include, but are not limited to, C6-C16 lower alkanes, non-silicone oils of animal, plant, animal or synthetic origin, fatty alcohols, fatty acids, esters of a fatty acid and/or of a fatty alcohol, non-silicone waxes, and silicones.

In some embodiments, the fatty alcohols, fatty esters, and fatty acids comprise at least one linear or branched, saturated or unsaturated hydrocarbon-based group shaving 6 to 30 carbon atoms, which is optionally substituted with at least one hydroxyl group. If they are unsaturated, those compounds may comprise one to three conjugated or nonconjugated carbon-carbon double bonds.

In some embodiments, the lower C6-C16 alkanes are linear. In some embodiments, the lower C6-C16 alkanes are branched. In some embodiments, the lower C6-C16 alkanes are cyclic. By way of non-limiting example, the lower C6-C16 alkanes may be chosen from hexane, undecane, dodecane, tridecane, and isoparaffins (for instance isohexadecane and isodecane).

Exemplary non-silicone oils of animal, plant, mineral, or synthetic origin that may be used in the compositions described herein include but are not limited to:

hydrocarbon-based oils of animal origin, such as perhydrosqualene;

triglyceride oils of plant or synthetic origin, such as liquid fatty acid triglycerides having from 6 to 30 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812, and 818 by the company Dynamit Nobel, jojoba oil, and shea butter oil;

linear or branched hydrocarbons having more than 16 carbon atoms, of mineral or synthetic origin, such as volatile or nonvolatile liquid paraffins, and derivatives thereof, petroleum jelly, liquid petroleum jelly, polydecenes, hydrogenated polyisobutenes such as PARLEAM®, liquid paraffins, petroleum jelly, liquid petroleum jelly, polydecenes, hydrogenated polyisobutenes such as PARLEAM®;

fluoro oils, perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

Exemplary fatty alcohols that may be used in the aqueous cosmetic composition (A) include, but are not limited to, linear or branched, saturated or unsaturated fatty alcohols having from 6 to 30 carbon atoms or from 8 to 30 carbon atoms, for instance cetyl alcohol, stearyl alcohol, and the mixture thereof (cetylstearyl alcohol), octyldodecanol, 2-butyloctanol, 2-hexyldecanol, 2-undecylpentadecanol, oleyl alcohol, and linoleyl alcohol.

Exemplary fatty acids that may be used in the aqueous cosmetic composition (A) include, but are not limited to, saturated or unsaturated carboxylic acids and have from 6 to 30 carbon atoms or from 9 to 30 carbon atoms, myristic acid, palmitic acid, stearic acid, behenic acid, oleic acid, linoleic acid, linolenic acid, and isostearic acid.

Exemplary esters of fatty acid and/or of fatty alcohol that may be used in the composition (A) include, but are not limited to, the esters of saturated or unsaturated, linear or branched C1-C26 aliphatic mono- or polyacids and of saturated or unsaturated, linear or branched C1-C26 aliphatic mono- or polyalcohols. In some embodiments, the total carbon number of the esters is greater than or equal to 10.

Exemplary monoesters include but are not limited to dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, and 2-hexyldecyl laurate.

Other exemplary esters include, but are not limited to, esters of C4-C22 dicarboxylic or tricarboxylic acids and of C1-C22 alcohols, and esters of mono-, di- or tricarboxylic acids and of C2-C26 di-, tri-, tetra- or pentahydroxy alcohols.

Other exemplary esters include, but are not limited to: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; polyethylene glycol distearates ethyl, isopropyl, myristyl, cetyl or stearyl palmitate; 2-ethylhexyl palmitate; 2-octyldecyl palmitate; alkyl myristates such as isopropyl, butyl, cetyl or 2-octyldodecyl myristate; hexyl stearate; butyl stearate; isobutyl stearate; dioctyl malate; hexyl laurate; 2-hexyldecyl laurate; and isononyl isononanoate or cetyl octanoate.

Composition (A) may further comprise, fatty ester, sugar esters, and diesters of C6-C30 or C12-C22 fatty acids. The term "sugar" includes oxygen-bearing hydrocarbon-based compounds having several alcohol functions, with or without aldehyde or ketone functions, and having at least 4 carbon atoms. Those sugars may be monosaccharides, oligosaccharides, or polysaccharides.

Exemplary sugars include, but are not limited to, sucrose (or saccharose), glucose, galactose, ribose, fucose, maltose, mannose, arabinose, xylose and lactose, and derivatives thereof, including alkyl derivatives, such as methyl derivatives, for instance methylglucose.

The sugar esters of fatty acids may be chosen from the group comprising the esters or mixtures of esters of sugars described previously and of linear or branched, saturated or unsaturated C6-C30 fatty acids. If they are unsaturated, those compounds may comprise, in some embodiments, one to three conjugated or nonconjugated carbon-carbon double bonds.

Exemplary esters may be chosen from mono-, di-, tri-, tetraesters and polyesters, and mixtures thereof.

Exemplary esters may also include, but are not limited to, oleates, laurates, palmitates, myristates, behenates, cocoates, stearates, linoleates, linolenates, caprates and arachidonates, or mixtures thereof such as, such as oleo-palmitate, oleo-stearate, and palmito-stearate mixed esters.

Monoesters and diesters and for example, sucrose, glucose or methylglucose mono- or dioleates, stearates, behenates, oleopalmitates, linoleates, linolenates and oleo-stearates may also be used.

An example that may be mentioned is the product sold under the name Glucate® DO by the company Amerchol, which is a methylglucose dioleate.

Exemplary esters or mixtures of esters of sugar and of fatty acid include, but are not limited to:

the products sold under the names F160, F140, F110, F90, F70, and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% di-triester-polyester;

the sucrose mono-dipalmito-stearate sold by the company Goldschmidt under the name TEGOSOFT® PSE.

Exemplary non-silicone waxes that may be used in the aqueous cosmetic composition (A) include, but are not limited to, carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used are marine waxes such as the product sold by the company Sophim under the reference M82, polyethylene waxes, and polyolefin waxes.

The silicones that may be used in the aqueous cosmetic composition (A) described herein are volatile or nonvolatile, cyclic, linear or branched silicones, which are unmodified or modified with organic groups, having a viscosity from $5 \times 10^{-6}$ to 2.5 m2/s at 25° C.

The silicones that may be used in the composition (A) described herein may be in the form of oils, waxes, resins, or gums.

Exemplary silicones include, but are not limited to, polydialkylsiloxanes, such as polydimethylsiloxanes (PDMS), and organomodified polysiloxanes comprising at least one functional group chosen from poly(oxyalkylene) groups, amino groups, and alkoxy groups.

The organopolysiloxanes are defined in greater detail in Walter Noll's "Chemistry and Technology of Silicones" (1968) Academic Press. They can be volatile or nonvolatile.

Exemplary volatile silicones include, but are not limited to, those having a boiling point ranging from 60° C. to 260° C., including:

(i) cyclic polydialkylsiloxanes having from 3 to 7 or 4 to 5 silicon atoms, such as octamethylcyclotetrasiloxane sold under the name VOLATILE SILICONE® 7207 by Union Carbide or SILBIONE® 70045 V 2 by Rhodia, decamethylcyclopentasiloxane sold under the name VOLATILE SILICONE® 7158 by Union Carbide, and Silbione® 70045 V 5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

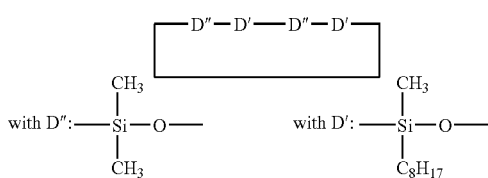

Mention may also be made of mixtures of cyclic polydialkylsiloxanes with organosilicon compounds, such as the mixture of octamethylcyclotetrasiloxane and tetra-trimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes having 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in COSMETICS AND TOILETRIES, Vol. 91, Jan. 76, pp. 27-32, Todd & Byers "Volatile Silicone Fluids for Cosmetics."

Nonvolatile polydialkylsiloxanes, polydialkylsiloxane gums and resins, polyorganosiloxanes modified with organofunctional groups above, and mixtures thereof, may be used.

Exemplary silicones include, but are not limited to, polydialkylsiloxanes, such as polydimethylsiloxanes having trimethylsilyl end groups. The viscosity of the silicones is measured, for example, at 25° C. according to ASTM standard 445 Appendix C.

Among these polydialkylsiloxanes, mention may be made, in a nonlimiting manner, of the following commercial products:

the SILBIONE® oils of the 47 and 70 047 series or the MIRASIL® oils sold by Rhodia, for instance the oil 70 047 V 500 000;
the oils of the MIRASIL® series sold by the company Rhodia;
the oils of the 200 series from the company Dow Corning, such as DC200 with a viscosity of 60,000 mm$^2$/s;
the VISCASIL® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C1-C20)dialkylsiloxanes.

Exemplary silicone gums that can be used include but are not limited to polydialkylsiloxanes, such as polydimethylsiloxanes with high number-average molecular masses ranging from 200,000 to 1,000,000, used alone or as a mixture in a solvent. Exemplary solvent include, but are not limited to, volatile silicones, polydimethylsiloxane (PDMS) oils, polyphenylmethylsiloxane (PPMS) oils, isoparaffins, polyisobutylenes, methylene chloride, pentane, dodecane, tridecane, and mixtures thereof.

Exemplary mixtures include, but are not limited to:
mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500,000, dissolved in the oil SF 1202 SILICONE FLUID corresponding to decamethylcyclopentasiloxane;
mixtures of two PDMSs with different viscosities, including mixtures of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6\ 2}$/s. This product may comprise 15% SE 30 gum and 85% SF 96 oil.

The organopolysiloxane resins include crosslinked siloxane systems having the following units:

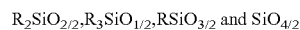

in which R represents a hydrocarbon-based group having 1 to 16 carbon atoms. In some embodiments, R denotes a $C_1$-$C_4$ lower alkyl radical, such as methyl.

Among those resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of the trimethyl siloxysilicate type resins sold, for instance, under the names X22-4914, X21-5034, and X21-5037 by the company Shin-Etsu.

The organomodified silicones are silicones as described above and comprising in their structure at least one organofunctional group attached via a hydrocarbon-based radical.

Besides the silicones described above, the organomodified silicones may be polydiarylsiloxanes, including polydiphenylsiloxanes, and polyalkylarylsiloxanes functionalized with organofunctional groups.

The polyalkylarylsiloxanes may be chosen from linear and/or branched polydimethyl/methylphenylsiloxanes and polydimethyl/diphenylsiloxanes with a viscosity of from $1 \times 10^{-5}$ to $5 \times 10^{-2}$ m2/s at 25° C.

Exemplary polyalkylarylsiloxanes include, but are not limited to, the products sold under the following names:
the SILBIONE® oils of the 70 641 series from Rhodia;
the oils of the RHODOURSIL® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may be made of polyorganosiloxanes comprising:
polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the $(C_{12})$alkylmethicone copolyol sold by the company Dow Corning under the name Q2 5200;
substituted or unsubstituted amine groups, such as the products sold under the name GP 4 Silicone Fluid and GP 7100 by the company Genesee, or the products sold under the names Q2 8220 and DOW CORNING 929 or 939 by the company Dow Corning. The substituted amine groups are, in particular, $C_1$-$C_4$ aminoalkyl groups;

alkoxylated groups such as the product sold under the name SILICONE COPOLYMER F-755 by SWS Silicones, and ABIL WAX® 2428, 2434 and 2440 by the company Goldschmidt.

In some embodiments, the at least one fatty substance does not comprise C2-C3 oxyalkylene units or glycerolated units.

In some embodiments, the at least one fatty substance is chosen from compounds that are liquid or pasty at room temperature and at atmospheric pressure.

In some embodiments, the at least one fatty substance is a compound that is liquid at a temperature of 25° C. and at atmospheric pressure.

In some embodiments, the at least one fatty substance is not a fatty acid.

Exemplary fatty substances include but are not limited to C6-C16 lower alkanes, fatty alcohols, esters of a fatty acid and/or of a fatty alcohol, non-silicone oils of mineral, plant or synthetic origin, and silicones.

In some embodiments, the at least one fatty substance is chosen from liquid petroleum jelly, polydecenes, fatty acid and/or fatty alcohol esters, liquid esters, or mixtures thereof.

In some embodiments, the at least one the fatty substance is non-silicone.

The aqueous composition (A) comprises at least 20% fatty substance. In some embodiments, the at least one fatty substance is present in aqueous composition (A) in a range from 25% to 80% of the total weight of the composition. In some embodiments, the at least one fatty substance is present in aqueous composition (A) in a range from 25% to 65% of the total weight of the composition. In some embodiments, the at least one fatty substance is present in aqueous composition (A) in a range from 30% to 55% of the total weight of the composition.

The aqueous cosmetic composition (A) also comprises at least one surfactant.

In some embodiments, the at least one surfactant is chosen from nonionic surfactants and anionic surfactants.

Exemplary anionic surfactants include, but are not limited to, the salts (in particular alkali metal salts, for example, sodium salts, ammonium salts, amine salts such as aminoalcohol salts or alkaline-earth metal salts such as magnesium salts) of the following compounds:
alkyl sulfates, alkyl ether sulfates, alkylamido ether sulfates, alkylaryl polyether sulfates, monoglyceride sulfates;
alkylsulfonates, alkylamidesulfonates, alkylarylsulfonates, α-olefin sulfonates, paraffin sulfonates;
alkyl phosphates, alkyl ether phosphates;
alkylsulfosuccinates, alkyl ether sulfosuccinates, alkylamidesulfosuccinates; alkylsulfosuccinamates;
alkylsulfoacetates;
acylsarcosinates; acylisethionates and N-acyltaurates;
salts of fatty acids such as oleic acid, ricinoleic acid, palmitic acid or stearic acid, coconut oil acid or hydrogenated coconut oil acid;
alkyl-D-galactoside uronic acid salts;
acyllactylates;
salts of polyoxyalkylenated alkyl ether carboxylic acids, of polyoxyalkylenated alkylaryl ether carboxylic acids or of polyoxyalkylenated alkylamido ether carboxylic acids, in particular those having from 2 to 50 ethylene oxide groups;
and mixtures thereof.

The alkyl or acyl radical of those various compounds may have from 6 to 24 carbon atoms or from 8 to 24 carbon atoms, and the aryl radical may denote a phenyl or benzyl group.

Exemplary nonionic surfactants include, but are not limited to, monooxyalkylenated or polyoxyalkylenated, monoglycerolated or polyglycerolated nonionic surfactants. The oxyalkylene units may be oxyethylene or oxypropylene units, or a combination thereof. In some embodiments, the oxyalkylene units are oxyethylene units.

Exemplary oxyalkylenated nonionic surfactants include, but are not limited to:
oxyalkylenated ($C_8$-$C_{24}$)alkylphenols,
saturated or unsaturated, linear or branched, oxyalkylenated $C_8$-$C_{30}$ alcohols,
saturated or unsaturated, linear or branched, oxyalkylenated $C_8$-$C_{30}$ amides,
esters of saturated or unsaturated, linear or branched, $C_8$-$C_{30}$ acids and of polyethylene glycols,
polyoxyethylenated esters of saturated or unsaturated, linear or branched, $C_8$-$C_{30}$ acids and of sorbitol,
saturated or unsaturated, oxyethylenated plant oils,
condensates of ethylene oxide and/or of propylene oxide, inter alia,
alone or as a mixture.

The at least one surfactant may comprise a number of moles of ethylene oxide and/or of propylene oxide ranging from 1 to 100 or ranging from 2 to 50. In some embodiments, the nonionic surfactants do not comprise any oxypropylene units.

In some embodiments, the oxyalkylenated nonionic surfactants are chosen from oxyethylenated C8-C30 alcohols, polyoxyethylenated linear or branched, saturated or unsaturated C8-C30 acid esters, and polyoxyethylenated sorbitol esters.

As examples of monoglycerolated or polyglycerolated nonionic surfactants, monoglycerolated or polyglycerolated C8-C40 alcohols may be used.

In some embodiments, the monoglycerolated or polyglycerolated C8-C40 alcohols correspond to the following formula:

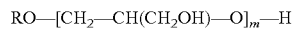

RO—[CH$_2$—CH(CH$_2$OH)—O]$_m$—H in which R represents a linear or branched $C_8$-$C_{40}$ alkyl or alkenyl radical, and m represents a number ranging from 1 to 30. In some embodiments, m represents a number ranging from 1 to 10.

Exemplary compounds that are suitable for use in the compositions described herein include, but are not limited to, lauryl alcohol having 4 mol of glycerol (INCI name: Polyglyceryl-4 Lauryl Ether), lauryl alcohol having 1.5 mol of glycerol, oleyl alcohol having 4 mol of glycerol (INCI name: Polyglyceryl-4 Oleyl Ether), oleyl alcohol having 2 mol of glycerol (INCI name: Polyglyceryl-2 Oleyl Ether), cetearyl alcohol having 2 mol of glycerol, cetearyl alcohol having 6 mol of glycerol, oleocetyl alcohol having 6 mol of glycerol, and octadecanol having 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, the C8/C10 alcohol having 1 mol of glycerol, the C10/C12 alcohol having 1 mol of glycerol, and the C12 alcohol having 1.5 mol of glycerol may be used.

In some embodiments, the at least one surfactant present in the composition is a nonionic surfactant.

In some embodiments, the at least one surfactant is present in the composition in an amount ranging from 0.1% to 50% by weight relative to the weight of the composition. In some embodiments, the at least one surfactant is present in the composition in an amount ranging from 0.5% to 30% by weight relative to the weight of the composition.

The aqueous cosmetic composition (A) may also comprise at least one adjuvant such as anionic, cationic, nonionic, amphoteric, or zwitterionic polymers or mixtures thereof; mineral thickeners, and fillers such as clays, talc; organic thickeners with, for instance, anionic, cationic, nonionic, and amphoteric polymeric associative thickeners; antioxidants; penetrants; sequestrants; fragrances; dispersants; film-forming agents; ceramides; preserving agents; and opacifiers.

In some embodiments, the at least one adjuvant is present in an amount ranging from 0.01% and 20% by weight relative to the weight of composition (A).

In some embodiments, the aqueous composition (A) comprises at least one mineral thickener chosen from organophilic clays, fumed silicas, or mixtures thereof.

Exemplary organophilic clays include but are not limited to montmorillonite, bentonite, hectorite, attapulgite and sepiolite, and mixtures thereof. In some embodiments, the clay is a bentonite or a hectorite.

In some embodiments, the clay is modified with a chemical compound chosen from quaternary amines, tertiary amines, amine acetates, imidazolines, amine soaps, fatty sulfates, alkyl aryl sulfonates and amine oxides, and mixtures thereof.

Organophilic clays that may be mentioned include quaternium-18 bentonites such as those sold under the names Bentone 3, Bentone 38, and Bentone 38V by the company Rheox, Tixogel VP by the company United Catalyst, Claytone 34, Claytone 40, and Claytone XL by the company Southern Clay; stearalkonium bentonites such as those sold under the names Bentone 27 by the company Rheox, Tixogel LG by the company United Catalyst and Claytone AF and Claytone APA by the company Southern Clay; quaternium-18/benzalkonium bentonites such as those sold under the names Claytone HT and Claytone PS by the company Southern Clay; quatemium-18 hectorites such as those sold under the names Bentone Gel DOA, Bentone Gel ECO5, Bentone Gel EUG, Bentone Gel IPP, Bentone Gel ISD, Bentone Gel SS71, Bentone Gel VS8, and Bentone Gel VS38 by the company Rheox, and Simagel M and Simagel S1345 by the company Biophil.

The fumed silicas may be obtained by high-temperature hydrolysis of a volatile silicon compound in an oxhydric flame, producing a finely divided silica. This process may make it possible to obtain hydrophilic silicas having a large number of silanol groups at their surface. Such hydrophilic silicas are sold, for example, under the names Aerosil 1300, Aerosil 2000, Aerosil 2550, Aerosil 300® and Aerosil 380® by the company Degussa, and Cab-O-Sil HS-50, Cab-O-Sil EH-5®, Cab-O-Sil LM-1300, Cab-O-Sil MS-55® and Cab-O-Sil M-5® by the company Cabot.

It may be possible to chemically modify the surface of the silica via chemical reaction to reduce the number of silanol groups. In some embodiments, silanol groups are substituted with hydrophobic groups: a hydrophobic silica is then obtained.

The hydrophobic groups may be:
trimethylsiloxyl groups, which may be obtained by treating fumed silica in the presence of hexamethyldisilazane. Silicas thus treated are known as "Silica silylate" according to the CTFA (6th edition, 1995). They are sold, for example, under the references AEROSIL R812® by the company Degussa and CAB-O-SIL TS-530® by the company Cabot.

dimethylsilyloxyl or polydimethylsiloxane groups, which may be obtained by treating fumed silica in the presence of polydimethylsiloxane or dimethyldichlorosilane. Silicas thus treated are known as "Silica dimethyl silylate" according to the CTFA (6th edition, 1995). They are sold, for example, under the references AEROSIL R972® and AEROSIL R974® by the company Degussa, and CAB-O-SIL TS-610® and CAB-O-SIL TS-720® by the company Cabot.

The fumed silica may have a particle size that may be nanometric to micrometric, for example ranging from about 5 to 200 nanometers.

In some embodiments, the composition comprises a hectorite, an organomodified bentonite or a fumed silica. In some embodiments, the composition is modified In some embodiments, the composition additionally comprises at least one mineral thickener presents in an amount ranging from 1% to 30% by weight relative to the weight of the composition.

The composition may also comprise at least one organic thickener.

Exemplary thickeners may be chosen from fatty acid amides (coconut acid diethanolamide or monoethanolamide, oxyethylenated alkyl ether carboxylic acid monoethanolamide), polymeric thickeners such as cellulose-based thickeners (hydroxyethycellulose, hydroxypropylcellulose, carboxymethylcellulose), guar gum and derivatives thereof (hydroxypropyl guar), gums of microbial origin (xanthan gum, scleroglucan gum), crosslinked homopolymers of acrylic acid or of acrylamidopropanesulfonic acid and associative polymers (polymers comprising hydrophilic zones and hydrophobic zones with a fatty chain (alkyl or alkenyl having at least 10 carbon atoms) that are capable, in an aqueous medium, of reversibly associating with each other or with other molecules).

In some embodiments, the organic thickener is chosen from cellulose-based thickeners (hydroxyethycellulose, hydroxypropylcellulose, carboxymethylcellulose), guar gum and derivatives thereof (hydroxypropyl guar), gums of microbial origin (xanthan gum, scleroglucan gum), crosslinked homopolymers of acrylic acid or of acrylamido-propanesulfonic acid, and cellulose-based thickeners, such as hydroxyethylcellulose.

In some embodiments, the content of organic thickener ranges from 0.01% to 20% by weight of the composition. In some embodiments, the content of the organic thickener ranges from 0.1% to 5% by weight relative to the weight of the composition.

In some embodiments, the composition (A) is in the form of a gel or a cream.

In the case of a dyeing process, the process described herein may be performed in the presence of a cosmetic composition (B) comprising at least one oxidation dye, at least one direct dye, or mixtures thereof.

The oxidation dyes may be chosen from at least one oxidation base that may be combined with at least one coupler.

Exemplary oxidation bases include but are not limited to para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylene-diamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylaminoethyloxy-para-phenylenediamine, methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives, and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that may be used include the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-yl-pyrazolo[1,5-a]pyrid-3-ylamine, 2-[(3-aminopyrazolo[1,5-a]pyrid-5-yl)(2-hydroxy-ethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole and 3,5-diamino-4-(3-hydroxyethyl)amino-1-methylpyrazole, and the addition salts thereof. 4,5-Diamino-1-(β-methoxyethyl)pyrazole may also be used.

In some embodiments, a 4,5-diaminopyrazole is used. In some embodiments, a 4,5-diamino-1-(β-hydroxyethyl)pyrazole and/or a salt thereof is used.

Pyrazole derivatives that may also be mentioned include diamino-N,N-dihydropyrazolopyrazolones, and those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo-[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

In some embodiments, 2,3-Diamino-6,7-dihydro-1H,5H-pyrazolo[1,2-a]pyrazol-1-one and/or a salt thereof is used.

In some embodiments, 4,5-Diamino-1-(β-hydromethyl) pyrazole and/or 2,3-diamino-6,7-dihydro-1H,5H-pyrazolo [1,2-a]pyrazol-1-one and/or a salt may be used as heterocyclic bases.

The cosmetic composition (B) may optionally comprise at least one coupler.

Among these couplers, mention may be made of meta-phenylenediamines, meta-aminophenols, meta-diphenols, naphthalene-based couplers, heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino) 1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, hydroxyethyl) amino-3,4-methylenedioxybenzene, 2,6-bis(β-hydroxyethylamino)toluene, 6-hydroxyindoline, 2,6-dihydroxy-4-methylpyridine, 1-H-3-methylpyrazo-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers may be chosen from the addition salts with an acid such as the hydrochlorides, hydrobromides, sulfates, citrates, succinates, tartrates, lactates, tosylates, benzenesulfonates, phosphates, and acetates.

In some embodiments, the oxidation bases are each present in an amount ranging from 0.0001% to 10% by weight relative to the total weight of the composition. In some embodiments, the oxidation bases are each present in an amount ranging from 0.005% to 5% by weight relative to the total weight of the composition.

In some embodiments, the couplers are each present in an amount ranging from 0.0001% to 10% by weight relative to the total weight of the composition. In some embodiments, the couplers are each present in an amount ranging from 0.005% to 5% by weight relative to the total weight of the cosmetic composition (B).

As regards the direct dyes, those dyes may be chosen from ionic and nonionic species. In some embodiments, the dyes are chosen from cationic and nonionic species.

Examples of suitable direct dyes that may be mentioned include azo; methine; carbonyl; azine; nitro (hetero)aryl; tri(hetero)arylmethane; porphyrin; phthalocyanin direct dyes, and natural direct dyes, alone or as mixtures.

In some embodiments, the azo dyes comprise an —N═N— function, the two nitrogen atoms of which are not simultaneously engaged in a ring. However, it is not excluded for one of the two nitrogen atoms of the sequence —N═N— to be engaged in a ring.

The dyes of the methine family may be, in some embodiments, compounds comprising at least one sequence chosen from >C═C< and —N═C<, the two atoms of which are not simultaneously engaged in a ring. However, it is pointed out that one of the nitrogen or carbon atoms of the sequences may be engaged in a ring. In some embodiments, the dyes of this family are derived from compounds of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins, and hemicyanins.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, and coumarin.

As regards the dyes of the cyclic azine family, mention may be made of azine, xanthene, thioxanthene, fluorindine, acridine, (di)oxazine, (di)thiazine, and pyronin.

The nitro (hetero)aromatic dyes may be chosen from nitrobenzene or nitropyridine direct dyes.

As regards the dyes of porphyrin or phthalocyanin type, it is possible to use cationic or noncationic compounds, optionally comprising at least one metal or metal ion, for instance alkali metals, alkaline-earth metals, zinc, and silicon.

Exemplary direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in some embodiments, anthraquinone, naphthoquinone or benzoquinone direct dyes; azine; xanthene; triarylmethane; indoamine; indigoid; phthalocyanin direct dyes, porphyrins and natural direct dyes, alone or as mixtures.

These dyes may be monochromophoric dyes (i.e. comprising only one dye) or polychromophoric, including di- or trichromophoric; the chromophores possibly being identical or different, and from the same chemical family or otherwise. A polychromophoric dye may comprise several radicals each derived from a molecule that absorbs in the visible region ranging from 400 to 800 nm. Furthermore, this absorbance of the dye may not require any prior oxidation thereof, or combination with any other chemical species.

In the case of polychromophoric dyes, the chromophores may be connected together by means of at least one linker, which may be cationic or noncationic.

In some embodiments, the linker is a linear, branched or cyclic C1-C20 alkyl chain, optionally interrupted with at least one heteroatom (such as nitrogen or oxygen) and/or with at least one group comprising such an atom (CO, SO2), optionally interrupted with at least one heterocycle that may or may not be fused to a phenyl nucleus and comprising at least one quaternized nitrogen atom engaged in said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted C1-C15 alkyl groups; the linker not comprising any nitro, nitroso, or peroxy groups.

If the heterocycles or aromatic nuclei are substituted, they are substituted, for example, with at least one C1-C8 alkyl radical optionally substituted with a hydroxyl, C1-C2 alkoxy, C2-C4 hydroxyalkoxy, acetylamino, or amino group substituted with one or two C1-C4 alkyl radicals, optionally bearing at least one hydroxyl group, or the two radicals possibly forming, with the nitrogen atom to which they are attached, a 5- or 6-membered heterocycle optionally comprising another heteroatom identical to or different than nitrogen; a halogen atom; a hydroxyl group; a C1-C2 alkoxy radical; a C2-C4 hydroxyalkoxy radical; an amino radical; an amino radical substituted with one or two identical or different C1-C4 alkyl radicals optionally bearing at least one hydroxyl group.

Among the benzenic direct dyes, mention may be made in a nonlimiting manner of the following compounds:
1,4-diamino-2-nitrobenzene,
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene 1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-p-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-(β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo, azomethine, methane, and tetraazapentamethine direct dyes, mention may be made of the cationic dyes described in patent applications WO 95/15144, WO 95/01772 and EP 714 954; FR 2 189 006, FR 2 285 851, FR 2 140 205, EP 1 378 544, and EP 1 674 073.

Thus, mention may be made of the following dyes of formulae (I) to (IV), and the compounds of formulae (I) and (III):

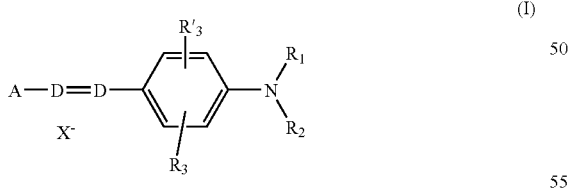

in which:
 D represents a nitrogen atom or a —CH group,
 $R_1$ and $R_2$, which may be identical or different, represent a hydrogen atom; a $C_1$-$C_4$ alkyl radical which may be substituted with a —CN, —OH or —NH$_2$ radical, or form, with a carbon atom of the benzene ring, a heterocycle optionally having oxygen or nitrogen, which may be substituted with at least one $C_1$-$C_4$ alkyl radical; a 4'-aminophenyl radical,
 $R_3$ and $R'_3$, which may be identical or different, represent a hydrogen atom or a halogen atom chosen from chlorine, bromine, iodine and fluorine, or a cyano, $C_1$-$C_4$ alkyl, $C_1$-$C_4$ alkoxy or acetyloxy radical,
 $X^-$ represents an anion that may be chosen from chloride, methyl sulfate, and acetate,
 A represents a group chosen from structures A1 to A18:

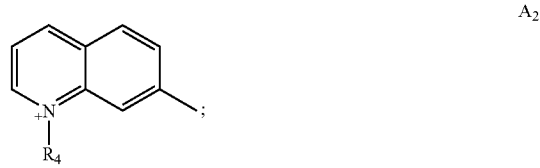

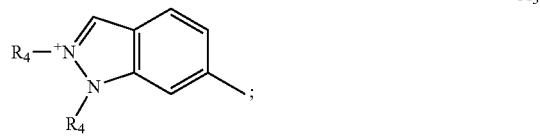

-continued

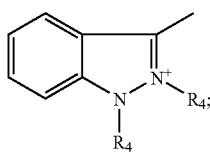
A10

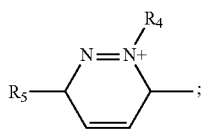
A11

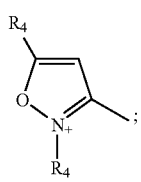
A12

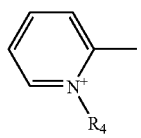
A13

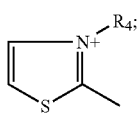
A14

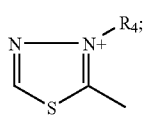
A15

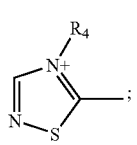
A16

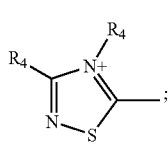
A17

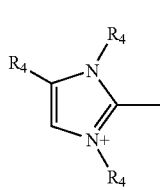
A18 in which $R_4$ represents a $C_1$-$C_4$ alkyl radical, which may be substituted with a hydroxyl radical and $R_5$ represents a $C_1$-$C_4$ alkoxy radical;

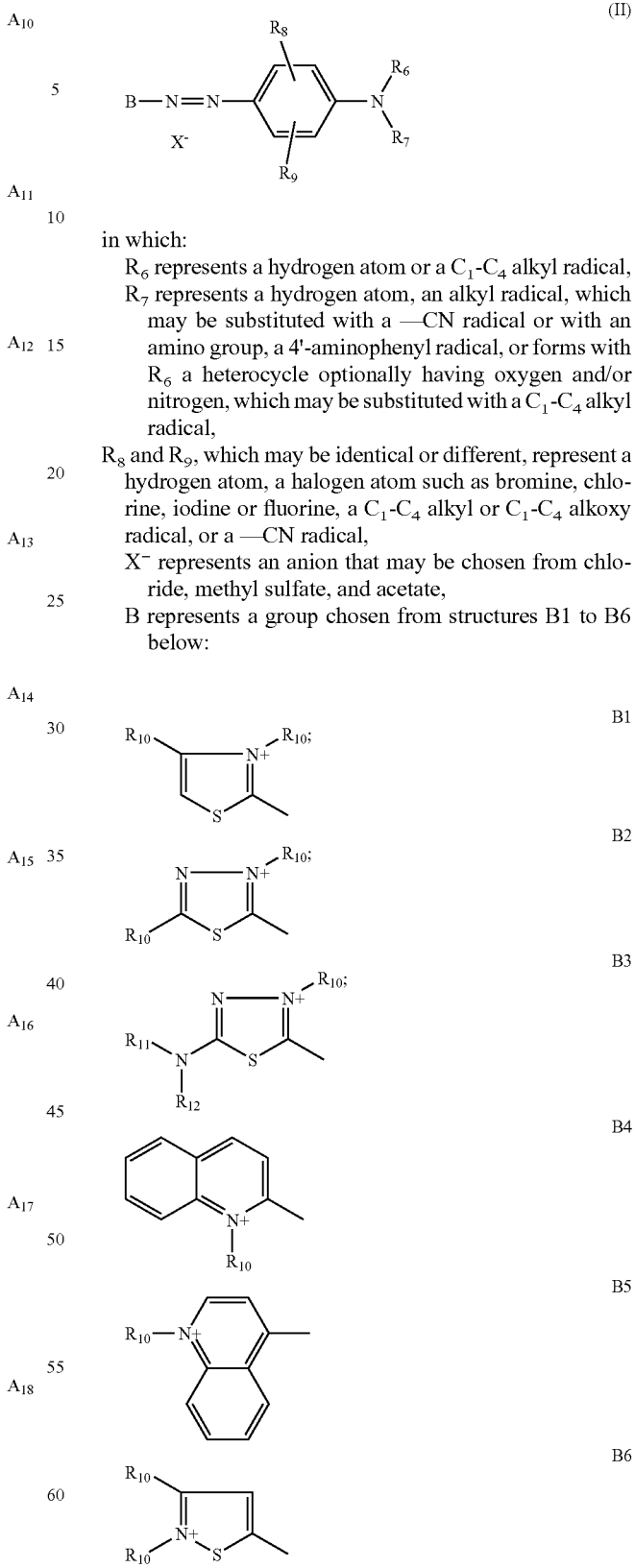

in which:
$R_6$ represents a hydrogen atom or a $C_1$-$C_4$ alkyl radical,
$R_7$ represents a hydrogen atom, an alkyl radical, which may be substituted with a —CN radical or with an amino group, a 4'-aminophenyl radical, or forms with $R_6$ a heterocycle optionally having oxygen and/or nitrogen, which may be substituted with a $C_1$-$C_4$ alkyl radical,
$R_8$ and $R_9$, which may be identical or different, represent a hydrogen atom, a halogen atom such as bromine, chlorine, iodine or fluorine, a $C_1$-$C_4$ alkyl or $C_1$-$C_4$ alkoxy radical, or a —CN radical,
$X^-$ represents an anion that may be chosen from chloride, methyl sulfate, and acetate,
B represents a group chosen from structures B1 to B6 below:

in which $R_{10}$ represents a $C_1$-$C_4$ alkyl radical, $R_{11}$ and $R_{12}$, which may be identical or different, represent a hydrogen atom or a $C_1$-$C_4$ alkyl radical;

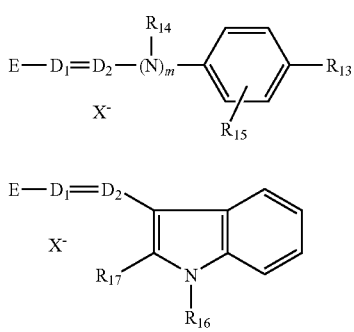
(III)

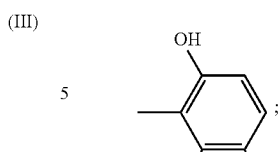
(III')

in which:
- $R_{13}$ represents a hydrogen atom, a $C_1$-$C_4$ alkoxy radical, a halogen atom such as bromine, chlorine, iodine or fluorine, or an amino radical,
- $R_{14}$ represents a hydrogen atom, a $C_1$-$C_4$ alkyl radical or forms, with a carbon atom of the benzene ring, a heterocycle optionally having oxygen and/or substituted with at least one $C_1$-$C_4$ alkyl group,
- $R_{15}$ represents a hydrogen atom or a halogen atom such as bromine, chlorine, iodine or fluorine,
- $R_{16}$ and $R_{17}$, which may be identical or different, represent a hydrogen atom or a $C_1$-$C_4$ alkyl radical,
- $D_1$ and $D_2$, which may be identical or different, represent a hydrogen atom or a —CH group,
- m=0 or 1, it being understood that when $R_{13}$ represents an unsubstituted amino group, then $D_1$ and $D_2$ simultaneously represent a —CH group and m=0,

- $X^-$ represents an anion that may be chosen from chloride, methyl sulfate, and acetate,
- E represents a group chosen from structures E1 to E8, below:

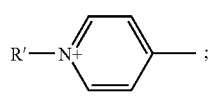
E1

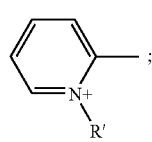
E2

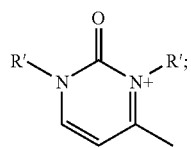
E3

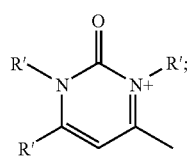
E4

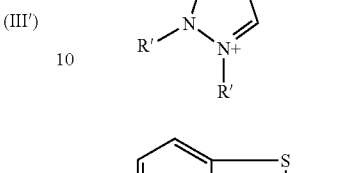
E5

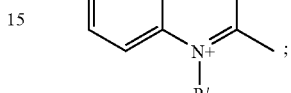
E6

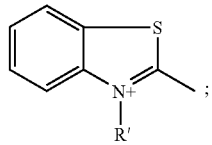
E7
and

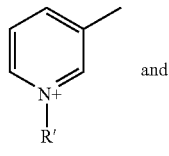
E8 in which R' represents a $C_1$-$C_4$ alkyl radical;

when m=0 and $D_1$ represents a nitrogen atom, then E may also denote a group of structure E9 below:

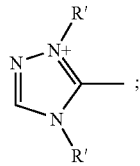
E9 in which R' represents a $C_1$-$C_4$ alkyl radical.

$$G-N=N-J \quad (IV)$$

in which:
the symbol G represents a group chosen from the structures $G_1$ to $G_3$ below:

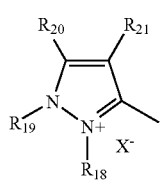
$G_1$

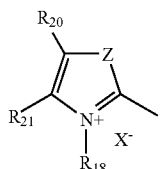

G₂

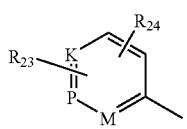

G₃ in which structures G₁ to G₃:

R₁₈ denotes a $C_1$-$C_4$ alkyl radical, a phenyl radical, which may be substituted with a $C_1$-$C_4$ alkyl radical, or a halogen atom chosen from chlorine, bromine, iodine, and fluorine;

R₁₉ denotes a $C_1$-$C_4$ alkyl radical or a phenyl radical;

R₂₀ and R₂₁, which may be identical or different, represent a $C_1$-$C_4$ alkyl radical, a phenyl radical, or form together in G₁ a benzene ring substituted with at least one $C_1$-$C_4$ alkyl, $C_1$-$C_4$ alkoxy, or NO₂ radical, or form together in G₂ a benzene ring optionally substituted with at least one $C_1$-$C_4$ alkyl, $C_1$-$C_4$ alkoxy, or NO₂ radicals;

R₂₀ may also denote a hydrogen atom;

Z represents an oxygen or sulfur atom or a group —NR₁₉;

M represents a group —CH, —CR(R denoting $C_1$-$C_4$ alkyl) or —NR₂₂(X⁻)ᵣ;

K represents a group —CH, —CR(R denoting $C_1$-$C_4$ alkyl) or —NR₂₂(X⁻)ᵣ;

P represents a group —CH, —CR(R denoting $C_1$-$C_4$ alkyl) or —NR₂₂(X⁻)ᵣ;

r denotes 0 or 1;

R₂₂ represents an O⁻ atom, a $C_1$-$C_4$ alkoxy radical or a $C_1$-$C_4$ alkyl radical;

R₂₃ and R₂₄, which may be identical or different, represent a hydrogen atom or a halogen atom chosen from chlorine, bromine, iodine, and fluorine, a $C_1$-$C_4$ alkyl or $C_1$-$C_4$ alkoxy radical, or an —NO₂ radical;

X⁻ represents an anion that may be chosen from chloride, iodide, methyl sulfate, ethyl sulfate, acetate, and perchlorate;

with the proviso that, if R₂₂ denotes O⁻, then r denotes zero;

if K or P or M denote —N—($C_1$-$C_4$)alkyl X⁻, then R₂₃ or R₂₄ may be different than a hydrogen atom;

if K denotes —NR₂₂(X⁻)ᵣ, then M=P=—CH, —CR;

if M denotes —NR₂₂(X⁻)ᵣ, then K=P=CH, —CR;

if P denotes —NR₂₂(X⁻)ᵣ, then K=M and denote —CH or —CR;

if Z denotes a sulfur atom with R₂₁ denoting $C_1$-$C_4$ alkyl, then R₂₀ is other than a hydrogen atom;

if Z denotes —NR₂₂ with R₁₉ denoting $C_1$-$C_4$ alkyl, then at least one of the radicals R₁₈, R₂₀ or R₂₁ of the group of structure G₂ is other than a $C_1$-$C_4$ alkyl radical;

the symbol J represents:

(a) a group of structure J₁ below:

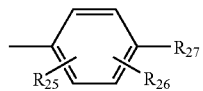

J₁ in which structure

R₂₅ represents a hydrogen atom, a halogen atom chosen from chlorine, bromine, iodine and fluorine, a $C_1$-$C_4$ alkyl or $C_1$-$C_4$ alkoxy radical, an —OH, —NO₂, —NHR₂₈, —NR₂₉R₃₀ or $C_1$-$C_4$—NHCOalkyl radical, or forms with R₂₆ a 5- or 6-membered ring optionally having at least one heteroatom chosen from nitrogen, oxygen, and sulfur;

R₂₆ represents a hydrogen atom, a halogen atom chosen from chlorine, bromine, iodine, and fluorine, a $C_1$-$C_4$ alkyl or $C_1$-$C_4$ alkoxy radical, or forms with R₂₇ or R₂₈ a 5- or 6-membered ring optionally having at least one heteroatom chosen from nitrogen, oxygen, and sulfur;

R₂₇ represents a hydrogen atom, an —OH radical, a radical —NHR₂₈ or a radical —NR₂₉R₃₀;

R₂₈ represents a hydrogen atom, a $C_1$-$C_4$ alkyl radical, a $C_1$-$C_4$ monohydroxyalkyl, $C_2$-$C_4$ polyhydroxyalkyl radical or a phenyl radical;

R₂₉ and R₃₀, which may be identical or different, represent a $C_1$-$C_4$ alkyl radical, a $C_1$-$C_4$ monohydroxyalkyl or $C_2$-$C_4$ polyhydroxyalkyl radical;

(b) a 5- or 6-membered nitrogenous heterocyclic group, which may comprise other heteroatoms and/or carbonyl groups and may be substituted with at least one $C_1$-$C_4$ alkyl, amino or phenyl radical, including a group of structure J₂ below:

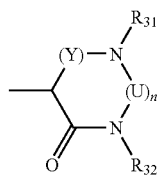

J₂ in which structure J₂:

R₃₁ and R₃₂, which may be identical or different, represent a hydrogen atom, a $C_1$-$C_4$ alkyl radical or a phenyl radical;

Y denotes a —CO— radical or a

radical;

n=0 or 1, with, when n denotes 1, U denotes a —CO— radical.

In structures (I) to (IV) defined above, the $C_1$-$C_4$ alkyl or alkoxy group may denote methyl, ethyl, butyl, methoxy, or ethoxy.

In some embodiments, the compounds of formulae (I) and (III) are:

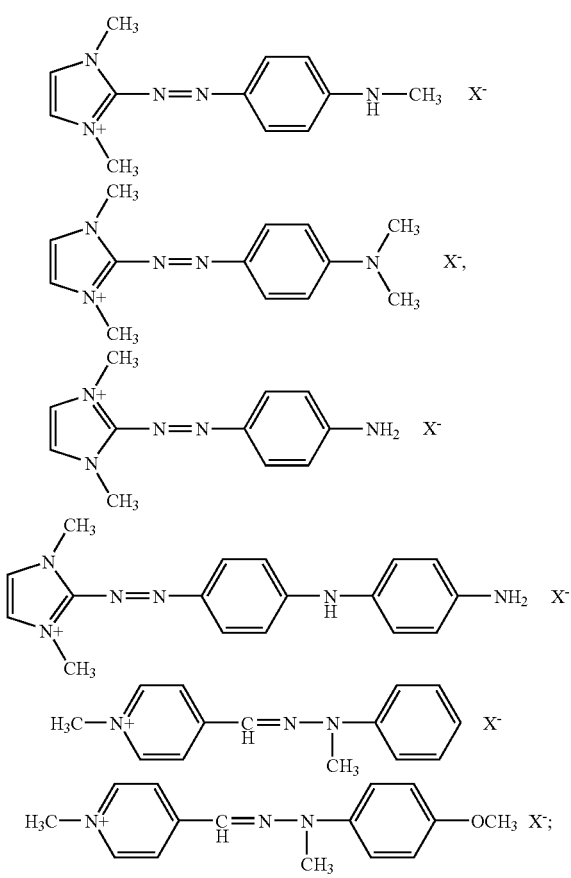

Among the azo direct dyes that may also be mentioned are the following dyes, described in the Colour Index International, 3rd edition:
Disperse Red 17
Basic Red 22
Basic Red 76
Basic Yellow 57
Basic Brown 16
Basic Brown 17
Disperse Black 9.

Mention may also be made of 1-(4'-aminodiphenylazo)-2-methyl-4-bis(β-hydroxyethyl)aminobenzene.

Among the quinone direct dyes that may be mentioned are the following dyes:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99
and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes that may be mentioned are the following compounds:
Basic Blue 17
Basic Red 2.

Among the triarylmethane dyes, mention may be made of the following compounds:
Basic Green 1
Basic Violet 3
Basic Violet 14
Basic Blue 7
Basic Blue 26.

Among the indoamine dyes, mention may be made of the following compounds:
2-β-hydroxyethylamino-5-[bis(β-4'-hydroxyethypamino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinone imine
3-N-(3'-chloro-4'-methylamino)phenylureido-6-methyl-1,4-benzoquinone imine
3-[4'-N-(ethyl,carbamylmethyl)amino]phenylureido-6-methyl-1,4-benzoquinone imine.

Among the dyes of tetraazapentamethine type, mention may be made of the following compounds given in the table below:

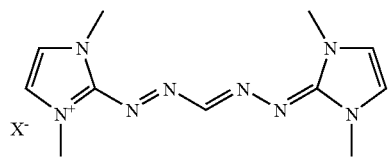

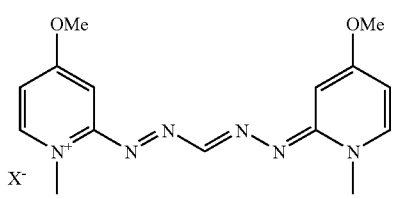

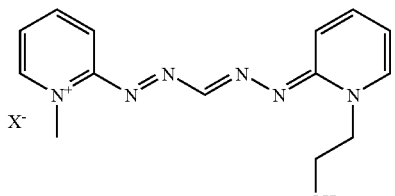

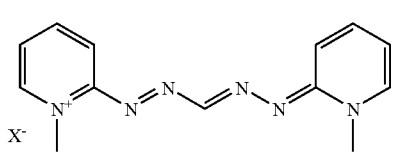

-continued

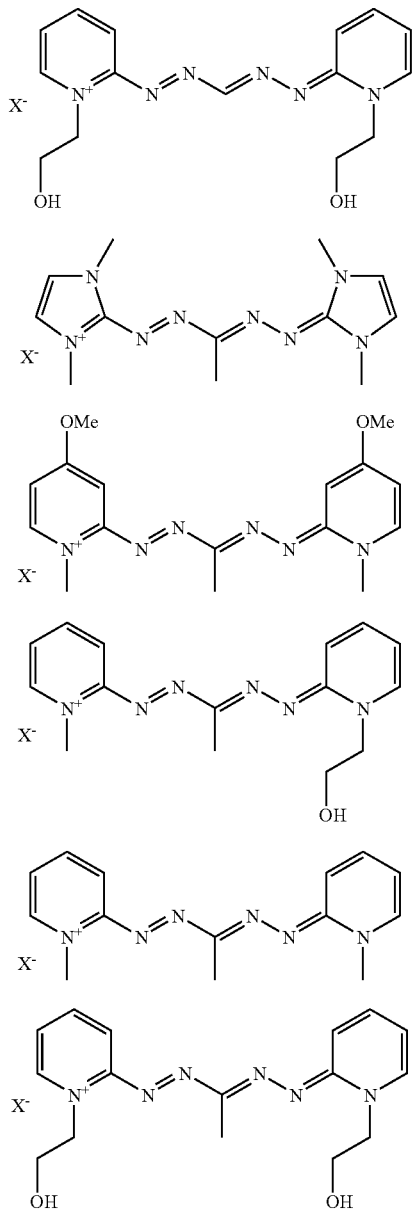

X⁻ represents an anion chosen from chloride, iodide, methyl sulfate, ethyl sulfate, acetate, and perchlorate.

Among the polychromophoric dyes, mention may be made of symmetrical or nonsymmetrical azo and/or azomethine (hydrazone) di- or trichromophoric dyes comprising, on the one hand, at least one optionally fused 5- or 6-membered aromatic heterocycle, comprising at least one quaternized nitrogen atom engaged in said heterocycle and optionally at least one other heteroatom (such as nitrogen, sulfur or oxygen), and, on the other hand, at least one optionally substituted phenyl or naphthyl group, optionally bearing at least one group OR with R representing a hydrogen atom, an optionally substituted C1-C6 alkyl radical, an optionally substituted phenyl nucleus, or at least one group N(R')2 with R', which may be identical or different, representing a hydrogen atom, an optionally substituted C1-C6 alkyl radical or an optionally substituted phenyl nucleus; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, a saturated 5- or 6-membered heterocycle.

Aromatic cationic heterocycles that may be mentioned include 5- or 6-membered rings having 1 to 3 nitrogen atoms, one being quaternized; said heterocycle moreover being optionally fused to a benzene nucleus. It should similarly be noted that the heterocycle may optionally comprise another heteroatom other than nitrogen, for instance sulfur or oxygen.

If the heterocycles or phenyl or naphthyl groups are substituted, they are substituted, for example, with at least one C1-C8 alkyl radical optionally substituted with a hydroxyl, C1-C2 alkoxy, C2-C4 hydroxyalkoxy, acetylamino or amino group substituted with one or two C1-C4 alkyl radicals optionally bearing at least one hydroxyl group, or the two radicals possibly forming, with the nitrogen atom to which they are attached, a 5- or 6-membered heterocycle, optionally comprising another heteroatom identical to or different than nitrogen; a halogen atom; a hydroxyl group; a C1-C2 alkoxy radical; a C2-C4 hydroxyalkoxy radical; an amino radical; an amino radical substituted with one or two identical or different C1-C4 alkyl radicals, optionally bearing at least one hydroxyl group.

These polychromophores may be, in some embodiments, connected together by means of at least one linker optionally comprising at least one quaternized nitrogen atom that may or may not be engaged in a saturated or unsaturated, optionally aromatic heterocycle.

Exemplary linkers may include, but are not limited to, a linear, branched or cyclic C1-C20 alkyl chain, optionally interrupted with at least one heteroatom (such as nitrogen or oxygen) and/or with at least one group comprising such a heteroatom (CO or SO2), optionally interrupted with at least one heterocycle that may or may not be fused to a phenyl nucleus and comprising at least one quaternized nitrogen atom engaged in said ring and optionally at least one other heteroatom (such as oxygen, nitrogen or sulfur), optionally interrupted with at least one substituted or unsubstituted phenyl or naphthyl group, optionally at least one quaternary ammonium group substituted with two optionally substituted C1-C15 alkyl groups; the linker not comprising any nitro, nitroso, or peroxy groups.

The bonding between the linker and each chromophore may take place, in some embodiments, via a heteroatom substituent on the phenyl or naphthyl nucleus or via the quaternized nitrogen atom of the cationic heterocycle.

The dye may comprise identical or different chromophores.

As examples of such dyes, reference may be made to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116, and EP 1 671 560.

It is also possible to use the cationic direct dyes mentioned in patent applications: EP 1 006 153, describing dyes comprising two chromophores of anthraquinone type connected via a linker of cationic type; EP 1 433 472, EP 1 433 474, EP 1 433 471 and EP 1 433 473, describing identical or different dichromophoric dyes, connected via a cationic or noncationic linker, and also EP 6 291 333, describing dyes comprising three chromophores, one of them being an anthraquinone chromophore, to which are attached two chromophores of azo or diazacarbocyanin type or an isomer thereof.

Among the natural direct dyes, mention may be made of lawsone, juglone, alizarin, purpurin, carminic acid, kermesic acid, purpurogallin, protocatechaldehyde, indigo, isatin, curcumin, spinulosin, apigenidin, and orceins. It is also possible to use extracts or decoctions comprising these natural dyes, such as henna-based poultices or extracts.

In some embodiments, the direct dyes are present in an amount ranging from 0.0001% to 10% by weight relative to the total weight of the composition. In some embodiments, the direct dyes are present in an amount ranging from 0.005% to 5% by weight relative to the total weight of the composition.

Cosmetic composition (B) may comprise one and/or the other types of dyes. In some embodiments, the cosmetic composition (B) may include a mixture of two dye compositions, one comprising at least one oxidation dye, and the other comprising at least one direct dye.

The cosmetic composition (B) also comprises at least one alkaline agent. In some embodiments, the at least one alkaline agent is chosen from organic amines and salts thereof, organic bases and ammonium salts.

The alkaline agent may be organic or mineral or hybrid.

A first type of alkaline agent is organic amines whose pKb at 25° C. is less than 12. In some embodiments, the pKb at 25° C. is less than 10. In some embodiments, the pKb at 25° C. is less than 6. In some embodiments, the pKb corresponds to the function of highest basicity.

In some embodiments, the organic amine may comprise a primary, secondary, or tertiary amine function, and at least one linear or branched C1-C8 alkyl group bearing at least one hydroxyl radical.

Organic amines may be, in some embodiments, chosen from alkanolamines such as mono-, di- or trialkanolamines, comprising one to three identical or different C1-C4 hydroxyalkyl radicals, may be used.

Among the compounds of this type that may be mentioned are monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

The organic amines having the following formula:

$$\begin{array}{c} Rx \\ \diagdown \\ N-W-N \\ \diagup \\ Ry \end{array} \begin{array}{c} Rz \\ \diagup \\ \diagdown \\ Rt \end{array}$$

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical, may also be suitable for use.

Examples of such amines that may be mentioned include 1,3-diaminopropane, 1,3-diamino-2-propanol, spermine, and spermidine.

According to some embodiments, the organic amine is chosen from amino acids.

The amino acids that may be used are of natural or synthetic origin, in L, D or racemic form, and comprise at least one acid function chosen from carboxylic acid, sulfonic acid, phosphonic acid, and phosphoric acid functions. The amino acids may be in their neutral or ionic form.

The amino acids may be chosen from basic amino acids comprising an additional amine function optionally included in a ring or in a ureido function.

Such basic amino acids may be chosen, in some embodiments, from those corresponding to formula (I) below:

$$R-CH_2-CH\begin{array}{c}NH_2\\ \diagdown \\ CO_2H\end{array} \quad (I)$$

in which R denotes a group chosen from:

imidazole group; —$(CH_2)_3NH_2$; —$(CH_2)_2NH_2$;

—$(CH_2)_2NHCONH_2$; —$(CH_2)_2NH-\underset{\underset{NH}{\parallel}}{C}-NH_2$

In some embodiments, the compounds corresponding to formula (I) are histidine, lysine, arginine, ornithine, and citrulline.

As amino acids, mention may be made of aspartic acid, glutamic acid, alanine, arginine, ornithine, citrulline, asparagine, carnitine, cysteine, glutamine, lysine, histidine, lysine, isoleucine, leucine, methionine, N-phenylalanine, proline, serine, taurine, threonine, tryptophan, tyrosine, and valine.

In some embodiments, the organic amine is chosen from basic amino acids. Exemplary amino acids include but are not limited to arginine, lysine, and histidine, and mixtures thereof.

In some embodiments, the organic amine is chosen from organic amines of heterocyclic type. Besides histidine that has already been mentioned in the amino acids, mention may be made in particular of pyridine, piperidine, imidazole, triazole, tetrazole, and benzimidazole.

In some embodiments, the organic amine is chosen from amino acid dipeptides. As amino acid dipeptides, mention may be made of carnosine, anserine, and baleine.

In some embodiments, the organic amine is chosen from compounds comprising a guanidine function. As amines of this type, mention may be made, apart from the arginine that has already been mentioned as an amino acid, of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

In some embodiments, the organic amine is an alkanolamine. In some embodiments, the organic amine is chosen from 2-amino-2-methyl-1-propanol, monoethanolamine, and mixtures thereof. In some embodiments, the organic amine is monoethanolamine.

A second type of alkaline agent includes organic or mineral salts (in this case, they are referred to as hybrid alkaline agents) of the organic amines as described above.

In some embodiments, the organic salts are chosen from the salts of organic acids such as citrates, lactates, glycolates, gluconates, acetates, propionates, fumarates, oxalates, and tartrates.

In some embodiments, the mineral salts are chosen from hydrohalides (for example hydrochlorides), carbonates, hydrogen carbonates, sulfates, hydrogen phosphates, and phosphates.

A third type of alkaline agent is mineral bases.

As used herein, the term "inorganic compound" may mean any compound bearing in its structure at least one element from columns 1 to 13 of the Periodic Table of the Elements other than hydrogen.

In some embodiments, the inorganic base comprises at least one element from columns 1 and 2 of the Periodic Table of the Elements other than hydrogen.

In some embodiments, the inorganic base has the following structure:

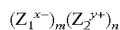

$$(Z_1^{x-})_m(Z_2^{y+})_n$$

in which:

Z$_2$ denotes a metal from columns 1 to 13 of the Periodic Table of the Elements, for instance sodium or potassium;

$Z_1^{x-}$ denotes an anion chosen from $CO_3^{2-}$, $OH^-$, $HCO_3^{2-}$, $SiO_3^{2-}$, $HPO_4^{2-}$, $PO_4^{3-}$ and $B_4O_7^{2-}$ ions;

x denotes 1, 2, or 3;

y denotes 1, 2, 3 or 4;

m and n denote, independently of each other, 1, 2, 3 or 4; with (n)(y)=(m)(x).

In some embodiments, the inorganic base corresponds to the following formula $(Z1x-)_m(Z2y+)_n$, in which Z2 denotes a metal from columns 1 and 2 of the Periodic Table of the Elements; Z1x− denotes an anion chosen from CO32−, OH— and SiO32− ions, x is 1, y denotes 1 or 2, and m and n independently of one another denote 1 or 2, with (n)(y)=(m)(x).

As inorganic bases, mention may be made of sodium carbonate, potassium carbonate, sodium hydroxide, potassium hydroxide, sodium metasilicate, and potassium metasilicate.

Another type of alkaline agent is ammonium salts.

The ammonium salts that may be used in composition (B), in some embodiments, are ammonium salts (NH4+).

The ammonium salts that may be used in composition (B) may be chosen, in some embodiments, from the following acid salts: acetate, carbonate, bicarbonate, chloride, citrate, nitrate, nitrite, phosphate, sulfate. In some embodiments, the salt is carbonate. In some embodiments, the salt is ammonium carbonate.

In some embodiments, composition (B) has an alkaline agents content ranging from 0.01% to 30% by weight relative to the weight of the composition. In some embodiments, composition (B) has an alkaline agents content ranging from 0.1% to 20% by weight relative to the weight of the composition.

In some embodiments, composition (B) does not comprise any aqueous ammonia as alkaline agent. In some embodiments, composition (B) comprises aqueous ammonia in an amount less than 0.03% by weight (expressed as NH3) relative to the weight of the final composition. In some embodiments, composition (B) comprises aqueous ammonia in an amount less than 0.01% by weight relative to the weight of the final composition.

The composition (B) may be an anhydrous or aqueous composition. In some embodiments, the term "aqueous composition" describes a composition comprising more than 5% by weight of water. In some embodiments, the term "aqueous composition" describes a composition comprising more than 10% by weight of water. In some embodiments, the term "aqueous composition" describes a composition comprising more than 20% by weight of water.

In some embodiments, the cosmetic composition (B) is an aqueous composition.

In some embodiments, composition (B) comprises water. In some embodiments, the water concentration ranges from 10% to 90% of the total weight of the composition. In some embodiments, the water concentration ranges from 20% to 80% of the total weight of the composition.

In some embodiments, the composition further comprises at least one solvent.

Examples of organic solvents that may be mentioned include linear or branched C2-C4 alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

In some embodiments, the at least one solvent is present in an amount ranging from 1% to 40% by weight relative to the weight of the cosmetic composition (B). In some embodiments, the at least one solvent is present in an amount ranging from 5% to 30% by weight relative to the weight of the cosmetic composition (B).

The cosmetic composition (B) may also comprise standard additives such as those that have been listed previously, and reference may be made thereto.

In some embodiments, the pH of the cosmetic composition (B) in aqueous form, ranges from 2 to 12. In some embodiments, the pH of the cosmetic composition (B) in aqueous form, ranges from 8 to 11. The pH may be adjusted by using acidifying or basifying agents.

Among the acidifying agents that may be mentioned, for example, are mineral or organic acids, for instance hydrochloric acid, orthophosphoric acid, sulfuric acid, carboxylic acids, for instance acetic acid, tartaric acid, citric acid or lactic acid, and sulfonic acids.

As regards the basifying agent, if it is present, it may be chosen, in some embodiments, from the non-salified organic amines described previously, or optionally aqueous ammonia. In some embodiments, the composition comprises aqueous ammonia or a salt thereof, and the content of basifying agent(s) is greater than the content of aqueous ammonia (expressed as NH3). In some embodiments, aqueous ammonia is used as basifying agent in composition (B), and the content of aqueous ammonia in the composition (B) is less than 0.03% by weight (expressed as NH3) relative to the weight of the final composition. In some embodiments, the content of aqueous ammonia in the composition (b) is less than 0.01% by weight relative to the weight of the final composition.

In some embodiments, the content of aqueous ammonia in the final composition is less than 0.03% by weight (expressed as NH3) relative to the weight of the final composition. In some embodiments, the content of aqueous ammonia in the final composition is less than 0.01% by weight (expressed as NH3) relative to the weight of the final composition.

It is indicated that the final composition results from the mixing of compositions (A), (B), and (C); those mixtures are prepared either before application to the keratin fibers (extemporaneous preparation) or directly on the keratin fibers (successive applications with or without premixing and without intermediate rinsing).

In some embodiments, the process is performed using a premix of compositions (A) and (B) or a preparation obtained extemporaneously by mixing together compositions (A), (B) and (C), and the interval between the mixing and the application to the hair is less than 30 minutes. In some embodiments, the process is performed using a premix of compositions (A) and (B) or a preparation obtained extemporaneously by mixing together compositions (A), (B) and (C), and the interval between the mixing and the application to the hair is less than 10 minutes. In some embodiments, the process is performed using a premix of compositions (A) and (B) or a preparation obtained extemporaneously by mixing together compositions (A), (B) and (C), and the interval between the mixing and the application to the hair is less than 5 minutes.

Finally, the process may be performed with a composition (C) comprising at least one oxidizing agent.

Exemplary oxidizing agents include, but are not limited to, hydrogen peroxide, urea peroxide, alkali metal bromates or ferricyanides, peroxygenated salts, for instance persulfates, perborates, alkali metal or alkaline-earth metal percarbonates, and also peracids and precursors thereof. At least one redox enzyme such as laccases, peroxidases, and 2-electron oxidoreductases (such as uricase), optionally in the presence of the respective donor or cofactor thereof, may also be used as the at least one oxidizing agent.

In some embodiments, the final composition does not contain any peracids and precursors thereof, peroxygenated salts, for instance persulfates, perborates or percarbonates of alkali metals or alkaline-earth metals.

In some embodiments, the at least one oxidizing agent is chosen from hydrogen peroxide, urea peroxide, alkali metal bromates, and ferricyanides.

In some embodiments, this oxidizing agent is formed from hydrogen peroxide, for example, in aqueous solution (aqueous hydrogen peroxide solution) whose concentration ranges from 0.1% to 50% by weight relative to the cosmetic composition (C). In some embodiments, this oxidizing agent is formed from hydrogen peroxide, for example, in aqueous solution (aqueous hydrogen peroxide solution) whose concentration ranges from 0.5% to 20% by weight relative to the cosmetic composition (C). In some embodiments, this oxidizing agent is formed from hydrogen peroxide, for example, in aqueous solution (aqueous hydrogen peroxide solution) whose concentration ranges from 1% to 15% by weight relative to the cosmetic composition (C)

Depending on the desired degree of lightening, the oxidizing agent may also comprise an oxidizing agent chosen from, for instance, peroxygenated salts.

The composition (C) may or may not be aqueous. The term "aqueous composition" describes a composition comprising more than 5% by weight of water. In some embodiments, the term "aqueous composition" describes a composition comprising more than 10% by weight of water. In some embodiments, the term "aqueous composition" describes a composition comprising more than 20% by weight of water.

In some embodiments, composition (C) is an aqueous composition.

In some embodiments, the composition (C) further comprises at least one organic solvent.

Examples of organic solvents that may be mentioned include linear or branched C2-C4 alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

In some embodiments, the at least one solvent is present in an amount ranging from 1% to 40% by weight of the cosmetic composition (C). In some embodiments, the at least one solvent is present in an amount ranging from 5% to 30% by weight of the composition (C).

In some embodiments, composition (C) may further comprise at least one acidifying agent described previously.

In some embodiments, the pH of the composition (C), when it is aqueous, is less than 7.

The composition (C) may also comprise other ingredients, for example, such as those detailed previously in the context of the aqueous composition (A) or of composition (B).

Finally, the oxidizing composition (C) may be in various forms, for instance in the form of a solution, an emulsion, or a gel.

In some embodiments, compositions (A), (B), and (C) are applied to wet or dry keratin fibers, successively and without intermediate rinsing. In some embodiments, compositions (A) then (B) and then (C) are applied to wet or dry keratin fibers, successively and without intermediate rinsing. In some embodiments, compositions (B) then (A) and then (C) are applied to wet or dry keratin fibers, successively and without intermediate rinsing.

In some embodiments, the composition resulting from the mixing, before application, of compositions (A) and (B), and then the oxidizing composition (C), are successively applied and without intermediate rinsing to the keratin fibers.

In some embodiments, a composition obtained by extemporaneous mixing, before application, of compositions (A), (B) and (C) is applied to the wet or dry keratin fibers.

In some embodiments, the interval between the mixing and application to the hair is less than 30 minutes. In some embodiments, the interval between the mixing and application to the hair is less than 10 minutes. In some embodiments, the interval between the mixing and application to the hair is less than 5 minutes.

In some embodiments, the weight ratios R1 of the amounts of compositions (A)+(B)/(C) and R2 of the amounts of compositions (A)/(B) ranging from 0.1 to 10. In some embodiments, the weight ratios R1 of the amounts of compositions (A)+(B)/(C) and R2 of the amounts of compositions (A)/(B) ranging from 0.3 to 3.

In some embodiments, the composition obtained after mixing of compositions (A), (B) and (C) is such that, after mixing, the content of fatty substances is greater than 20% weight relative to the total weight of the composition. In some embodiments, the composition obtained after mixing of compositions (A), (B) and (C) is such that, after mixing, the content of fatty substances is greater than 25% weight relative to the total weight of the composition. In some embodiments, the composition obtained after mixing of compositions (A), (B) and (C) is such that, after mixing, the content of fatty substances is greater than 30% weight relative to the total weight of the composition.

In some embodiments, the mixture present on the fibers (resulting either from the extemporaneous mixing of the compositions, or from the successive application of these compositions) is left in place for a time ranging from about 1 minute to 1 hour. In some embodiments, the mixture present on the fibers (resulting either from the extemporaneous mixing of the compositions, or from the successive application of these compositions) is left in place for a time ranging from about 5 minutes to 30 minutes. In some embodiments, the temperature during the process ranges from room temperature (for example, ranging from 15 to 25° C.) to 80° C. In some embodiments, the temperature during the process ranges from room temperature (for example, ranging from 15 to 25° C.) to 60° C.

In some embodiments, after the treatment, the human keratin fibers are optionally rinsed with water, optionally washed with a shampoo, and then rinsed with water, before being dried or left to dry.

Finally, also provided is a multi-compartment device comprising a first compartment comprising an aqueous composition (A), a second compartment comprising a cosmetic composition (B) comprising at least one alkaline agent and optionally at least one oxidation dye, at least one direct dye, or mixtures thereof, and a third compartment comprising a cosmetic composition (C) comprising at least one oxidizing agent.

The examples that follow serve to illustrate the disclosure without, however, being limiting in nature.

EXAMPLES

Exemplary Lightening Process

The following compositions were prepared in which the amounts are expressed in grams:

|  | A1 | A2 |
|---|---|---|
| Aqueous compositions (A): | | |
| Oxyethylenated (4 EO) sorbitan monolaurate | 21.7 | 21.7 |
| Fumed silica of hydrophobic nature | 11.1 | 11.1 |
| Demineralized water | 5 | 10 |
| Liquid petroleum jelly | qs 100 | qs 100 |
| Composition (B): | | |
| Pure monoethanolamine |  | 40 |
| Demineralized water |  | qs 100 |

The following were mixed together:
9 parts by weight of an aqueous composition A (A1 or A2),
1 part by weight of composition (B), and
parts by weight of 20 volume Platinium International oxidizing agent (6% hydrogen peroxide) (C).

The resulting mixture had a pH of 10±0.1. This mixture was applied to a natural lock (tone depth 4) according to a bath ratio "mixture/lock" of 10/1 (g/g).

The leave-on time was 30 minutes at room temperature (about 27° C.).

After this leave-on time, the lock was rinsed, and then washed with Elvive multivitamin shampoo.

Results

The color of the locks were evaluated in the CIE $L^* a^* b^*$ system using a Minolta CM2600D spectrophotometer.

The lightening of a lock ($\Delta Eab^*$) was evaluated in the CIE $L^* a^* b^*$ system. In this $L^* a^* b^*$ system, $L^*$ represents the intensity of the color, $a^*$ represents the green/red color axis and $b^*$ represents the blue/yellow color axis. The lower the value of $L^*$, the darker or more intense the color.

In the table below, the value of $\Delta Eab^*$ was calculated from the values of $L^* a^* b^*$ according to the following equation (i):

$$\Delta E_{ab}^* = \sqrt{(L^*-L_o^*)^2 + (a^*-a_o^*)^2 + (b^*-b_o^*)^2} \quad (i)$$

The lightening of a lock ($\Delta Eab^*$) was calculated on locks of natural hair of tone depth 4.

In equation (i), $L^*$, $a^*$ and $b^*$ represent the values measured on locks of natural hair of tone depth 4 after lightening treatment, and $L0^*$, $a0^*$ and $b0^*$ represent the values measured on untreated locks of natural hair of tone depth 4.

The greater the value of $\Delta Eab^*$, the greater the lightening (variation of color).

|  | $L^*$ | $a^*$ | $b^*$ | $\Delta E^*ab$ |
|---|---|---|---|---|
| Untreated natural lock (HT4) | 17.7 | 1.7 | 1.4 | — |
| Lock treated with the process described herein using composition A1 | 23 | 6.6 | 7.7 | 9.6 |
| Lock treated with the process described herein using composition A2 | 22.3 | 6.6 | 7.4 | 9 |

The table above shows that the process described herein performed with a composition comprising an alkaline agent other than aqueous ammonia made it possible to obtain lightening of the keratin fibers.

Example of a Dyeing Process

The following compositions were prepared (amounts expressed in grams)

|  | 100 g |
|---|---|
| Aqueous composition A: | |
| Oxyethylenated (4 EO) sorbitan monolaurate | 21.7 |
| Fumed silica of hydrophobic nature | 11.1 |
| Demineralized water | 10 |
| Liquid petroleum jelly | qs 100 |
| Cosmetic composition B: | |
| para-Phenylenediamine | 6.55 |
| Resorcinol | 4.95 |
| 2-Methylresorcinol | 1.86 |
| 1-β-Hydroxyethyloxy-2,4-diaminobenzene dihydrochloride | 0.15 |
| Sodium metabisulfite powder | 0.46 |
| Erythorbic acid | 0.31 |
| Monoethanolamine | 40.07 |
| Demineralized water | qs 100 |
| Composition (C) | |
| Fatty alcohols | 2.28 |
| Nonionic surfactants | 1.42 |
| Glycerol | 0.5 |
| Hydrogen peroxide | 6 |
| Hydrogen peroxide stabilizers | 0.12 |
| Demineralized water | qs 100 |

The following were mixed together:
9 parts by weight of the aqueous composition (A)
1 part by weight of composition (B)
10 parts by weight of the aqueous oxidizing composition (C) of pH equal to 2.3.

The mixture obtained, the pH of which was about 10 (±0.1), was then applied to a lock of natural hair containing 90% grey hairs (NG) and to a lock of permanent-waved hair containing 90% grey hairs (PWG). The "mixture/lock" bath ratio was, respectively, 10/1 (g/g).

The leave-on time was 30 minutes at 27° C. After this time, the locks were rinsed, and then washed with Elvive multivitamin shampoo.

Results

The color of the locks were evaluated in the CIE $L^* a^* b^*$ system, using a Minolta CM2600D spectrocolorimeter.

Calculation of the Selectivity

The value of $\Delta E$ (selectivity) was calculated from the values of $L^*$, $a^*$ and $b^*$ measured according to the following equation (ii):

$$\Delta E = \sqrt{(L^*-L_o^*)^2 + (a^*-a_o^*)^2 + (b^*-b_o^*)^2} \quad (i)$$

In equation (ii), $L^*$, $a^*$ and $b^*$ represent the values measured on dyed natural grey hair, and $L0^*$, $a0^*$ and $b0^*$ represent the values measured on locks of dyed permanent-waved grey hair.

The coloration selectivity ΔE corresponds to the variation in color between natural hair, representative of the nature of the hair at the root, and permanent-waved hair, which is representative of the nature of the hair at the end. The lower the value of ΔE, the more uniform the coloration between the end and the root of the hair.

The results are given in the table below.

| | L* | a* | b* | ΔE selectivity |
|---|---|---|---|---|
| Lock of natural hair treated with the composition described herein | 19.41 | 2.14 | 3.32 | 2.99 |
| Lock of permanent-waved hair treated with the composition described herein | 17.08 | 1.22 | 1.67 | |

As seen in the above table, strong and sparingly selective coloration were obtained with the process described herein.

Furthermore, no aggressive odor was observed, either during the preparation of the dye mixture, or during the leave-on time on the locks.

What is claimed is:

1. A process for lightening or dyeing keratin fibers, comprising applying to the fibers
   (a) an aqueous cosmetic composition (A) comprising at least one fatty substance and at least one surfactant;
   (b) a cosmetic composition (B) comprising at least one alkaline agent,
   (c) a composition (C) comprising at least one oxidizing agent,
   wherein the amount of the at least one fatty substance in composition (A) is greater than 20% by weight relative to the total weight of composition (A), and
   wherein when the process used is a process for dyeing keratin fibers, then cosmetic composition (B) further comprises at least one oxidation dye, at least one direct dye, or a mixture thereof.

2. Process according to claim 1, wherein the aqueous cosmetic composition (A) comprises more than 5% by weight of water.

3. Process according to claim 1, wherein the at least one fatty substance is chosen from compounds that are liquid or pasty at room temperature and at atmospheric pressure.

4. Process according to claim 1, wherein the at least one fatty substance is chosen from $C_6$-$C_{16}$ lower alkanes, non-silicone oils of animal, plant, mineral or synthetic origin fatty alcohols, fatty acids, fatty acid esters and/or fatty alcohol esters, non-silicone waxes, and silicones.

5. Process according claim 1, wherein the at least one fatty substance is chosen from liquid petroleum jelly, polydecenes, and liquid esters of fatty acids and/or of fatty alcohols, and mixtures thereof.

6. Process according to claim 1, wherein the at least one fatty substance is present in an amount of at least 20% by weight relative to the total weight of composition (A).

7. Process according to claim 1, wherein the aqueous composition (A) comprises at least one surfactant chosen from nonionic surfactants, such as monooxyalkylenated or polyoxyalkylenated, and monoglycerolated or polyglycerolated nonionic surfactants.

8. Process according to claim 1, wherein the at least one alkaline agent is chosen from organic amines and salts thereof, mineral bases and ammonium salts.

9. Process according to claim 7, wherein the at least one alkaline agent is monoethanolamine.

10. Process according to claim 1, wherein the at least one alkaline agent of composition (B) is present in an amount ranging from 0.01% to 30% by weight relative to the weight of the said composition (B).

11. Process according to claim 1, wherein the at least one oxidizing agent of aqueous composition (C) is chosen from hydrogen peroxide, urea peroxide, alkali metal bromates, and ferricyanides.

12. Process according to claim 1, wherein compositions (A), (B) and (C) are applied successively and without intermediate rinsing to the dry or wet keratin fibers.

13. Process according to claim 1, wherein the composition resulting from the mixing, before application, of compositions (A) and (B) and then the composition (C) is applied successively and without intermediate rinsing to the keratin fibers.

14. Process according to claim 1, wherein a composition obtained by extemporaneous mixing, before application, of compositions (A), (B) and (C), is applied to the dry or wet keratin fibers.

15. Multi-compartment device comprising
   a first compartment comprising an aqueous cosmetic composition (A) comprising at least one fatty substance and at least one surfactant,
   a second compartment comprising a cosmetic composition (B) comprising at least one alkaline agent and further comprising at least one oxidation dye, at least one direct dye, or mixtures thereof, and
   a third compartment containing a composition (C) comprising at least one oxidizing agent,
   wherein the amount of the at least one fatty substance in composition (A) is greater than 20% by weight relative to the total weight of composition (A).

* * * * *